(12) United States Patent
Abe et al.

(10) Patent No.: US 7,273,741 B2
(45) Date of Patent: Sep. 25, 2007

(54) COPPER TOLERANT YEAST AND PECTINASES PRODUCED BY THE YEAST

(75) Inventors: Fumiyoshi Abe, Yokosuka (JP); Koki Horikoshi, Yokosuka (JP)

(73) Assignee: Japan Agency for Marine-Earth Science and Technology, Yokosuka-shi (JP)

( * ) Notice: Subject to any disclaimer, the term of this patent is extended or adjusted under 35 U.S.C. 154(b) by 608 days.

(21) Appl. No.: 10/252,093

(22) Filed: Sep. 23, 2002

(65) Prior Publication Data

US 2003/0129734 A1 Jul. 10, 2003

Related U.S. Application Data

(63) Continuation of application No. PCT/JP01/02255, filed on Mar. 22, 2001.

(30) Foreign Application Priority Data

Mar. 24, 2000 (JP) ............................ 2000-083571

(51) Int. Cl.
- *C12N 9/26* (2006.01)
- *C12N 1/14* (2006.01)
- *C12N 1/20* (2006.01)
- *C08B 30/04* (2006.01)

(52) U.S. Cl. .............................. 435/201; 435/4; 435/6; 435/41; 435/69.1; 435/183; 435/200; 435/252.3; 435/254.1; 435/254.2; 435/243; 435/262; 435/275; 536/23.2

(58) Field of Classification Search .................... 435/4, 435/6, 69.1, 183, 200, 201–210, 252.3, 254.1, 435/254.2, 255.17; 536/23.2
See application file for complete search history.

(56) References Cited

OTHER PUBLICATIONS

Karel Grohmann et al., *Fermentation of Orange Peel Hydrolysates by Ethanologenic Escherichia coli*, Apppllied Biochemistry and Biotechnology, vol. 57/58, 1996, pp. 383-388.

Federico Federichi, *Production, Purification and Partial Chracterization of an Endo-polygalacturonase from Cryplococcus albidus var, albidus*, Antonie van Leeuwenhoek, vol. 51 No. 2, (1985), pp. 139-150.

Hirotsugu Imahara et al., *Effect of Copper on Growth of Yeast*, Agric. Biol. Chem., 42 (6), 1173-1179, 1978.

K. C. Gross, Hortscience, vol. 17, No. 6, pp. 933-934, "A Rapid and Sensitive Spectrophotometric Method for Assaying Polygalacturonase Using 2-Cyanoacetamide", 1982.

F. Federici, Boll. Soc. Ital. Biol. Sper., vol. 59, pp. 1509-1512, "Preliminary Study of the Pectolytic Activity of *Cryptococcus albidus* Var. Albidus", 1983.

A. M. McKay, FEMS Microbiology Letters 56, pp. 355-358, "A Plate Assay Method for the Detection on Fungal Polygalacturonase Secrection", 1988.

F. Abe, et al. JAMSTEC J. Deep Sea Res., vol. 14, pp. 573-580, "Characterization of Copper Tolerant Deep-Sea Yeast *Cryptococcus* SP. N6 Isolated From the Japan Trench", 1998 (with partial English translation).

T. Miura, et al., International Congress on Extremophiles '98, p. 334, "Isolated and Characterization of a Copper Tolerant Yeast *Cryptococcus* SP. From the Japan Trench", Jan. 18-22, 1998.

Program of the Annual Meeting 1999 of The Japan Society for Bioscience, Biotechnology, and Agrochemistry, vol. 73, No. 3, pp. 17, 54 and 34, Mar. 30-Apr. 1, 1999 (with English translation).

T. Miura, et al., Proceedings of 4th Symposium on Bio Nano Electronics, p. 74, "Purification and Characterization of Extracellular Endopolygalacturonases of the Copper Tolerant Yeast *Cryptococcus* SP. N6 Isolated From the Japan Trench", Nov. 15, 1999.

*Primary Examiner*—Manjunath Rao
(74) *Attorney, Agent, or Firm*—Oblon, Spivak, McClelland, Maier & Neustadt, P.C.

(57) ABSTRACT

The object of the present invention is to provide a yeast which is tolerant to copper and which can incorporate copper at a high concentration, and also a method of removing or recovering copper from extracellular solution. The present invention is copper-tolerant yeast and the pectinases produced by the yeast. Particularly, the present invention is copper-tolerant yeast *Cryptococcus* sp. N6 strain isolated from deep-sea sediments and the pectinases produced by the yeast.

9 Claims, 11 Drawing Sheets

FIG. 1
(A): *Cryptococcus* sp. N6
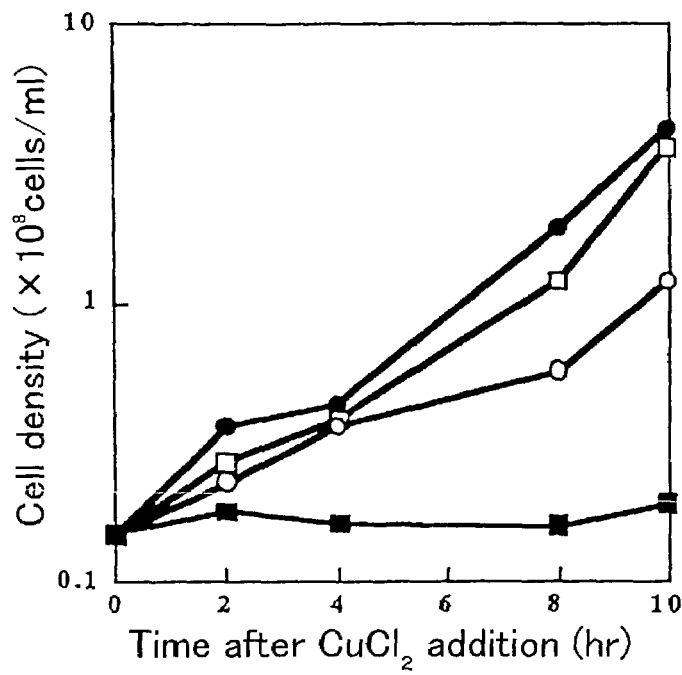
(B): *Cryptococcus albidus* IFO-0378
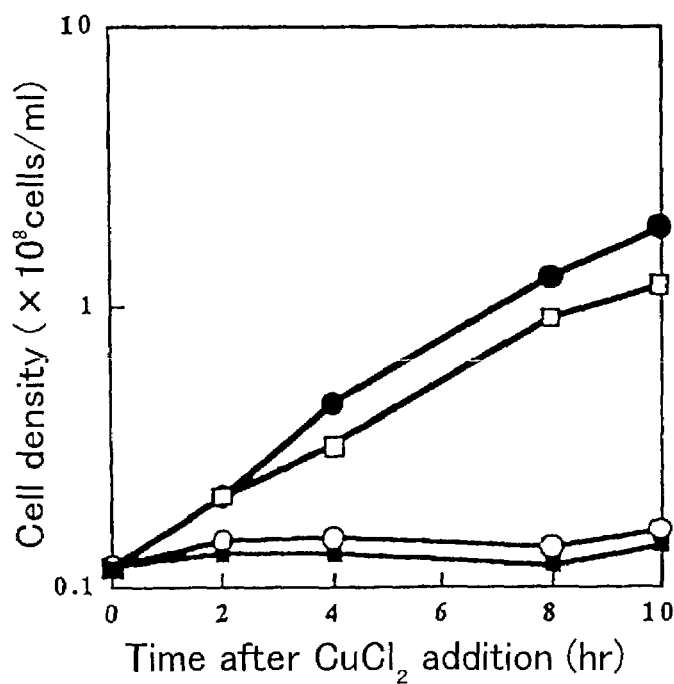

FIG. 2
(A) *Cryptococcus sp. N6*
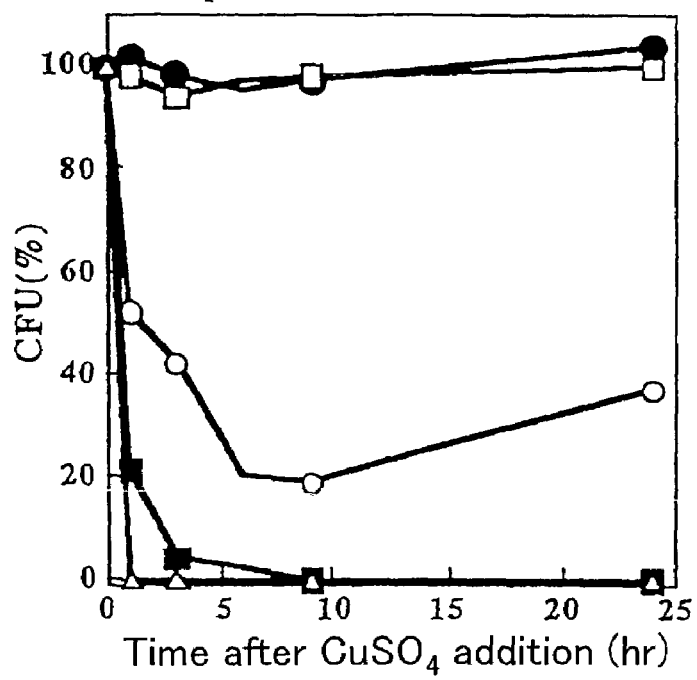
(B) *Cryptococcus albidus IFO-0378*
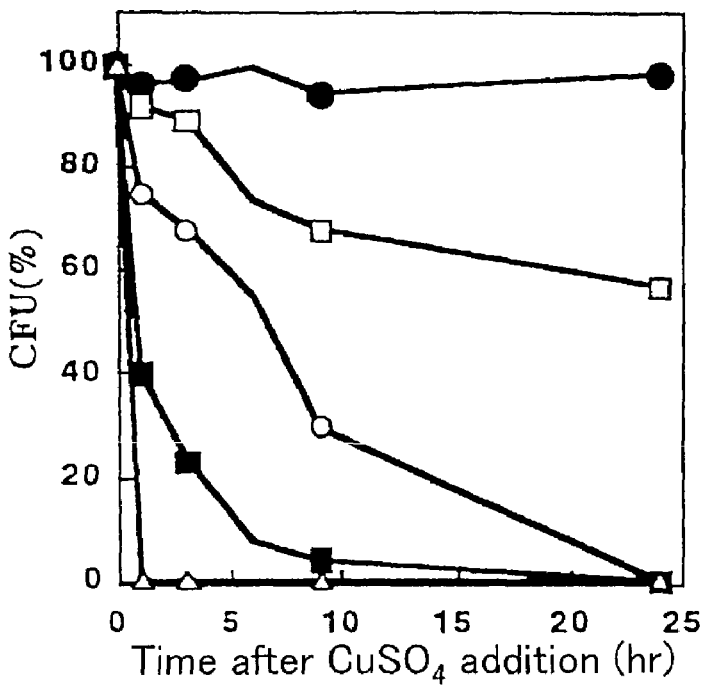

FIG. 11

(A) *Cryptococcus* sp. N6 p36 and p40

```
                              *TATISSY SDVAT AV SK*STV
                                      1       10      20
```

(B) *F. moniliforme* pgA

```
MVRNIVSRLCSQLFALPSSSLQERDPCSVTEY SGLAT AV SCKNIV LNGFQVPTGKQLDL
        10         20         30      40         50        60
```

* Not determined

SEQUENCE LISTING

<160> NUMBER OF SEQ ID NOS: 6

<210> SEQ ID NO 1
<211> LENGTH: 19
<212> TYPE: DNA
<213> ORGANISM: ARTIFICIAL SEQUENCE
<220> FEATURE:
<223> OTHER INFORMATION: SYNTHETIC DNA

<400> SEQUENCE: 1
gtagtcatat gcttgtctc                                            19

<210> SEQ ID NO 2
<211> LENGTH: 20
<212> TYPE: DNA
<213> ORGANISM: ARTIFICIAL SEQUENCE
<220> FEATURE:
<223> OTHER INFORMATION: SYNTHETIC DNA

<400> SEQUENCE: 2
tccgcaggtt cacctacgga                                           20

<210> SEQ ID NO 3
<211> LENGTH: 21
<212> TYPE: DNA
<213> ORGANISM: ARTIFICIAL SEQUENCE
<220> FEATURE:
<223> OTHER INFORMATION: SYNTHETIC DNA

<400> SEQUENCE: 3
ggctgctggc accagacttg c                                         21

<210> SEQ ID NO 4
<211> LENGTH: 21
<212> TYPE: DNA
<213> ORGANISM: ARTIFICIAL SEQUENCE
<220> FEATURE:
<223> OTHER INFORMATION: SYNTHETIC DNA

<400> SEQUENCE: 4

-continued

```
gcaagtctgg tgccagcagc c                                             21

<210> SEQ ID NO 5
<211> LENGTH: 24
<212> TYPE: DNA
<213> ORGANISM: ARTIFICIAL SEQUENCE
<220> FEATURE:
<223> OTHER INFORMATION: SYNTHETIC DNA

<400> SEQUENCE: 5
gaggcaataa caggtctgtg atgc                                          24

<210> SEQ ID NO 6
<211> LENGTH: 22
<212> TYPE: PRT
<213> ORGANISM: CRYPTOCOCCUS SP
<220> FEATURE:
<221> NAME/KEY: MISC_FEATURE
<222> LOCATION: (1)..(1)
<223> OTHER INFORMATION: X IS ANY ONE AMINO ACID
<220> FEATURE:
<221> NAME/KEY: MISC_FEATURE
<222> LOCATION: (19)..(19)
<223> OTHER INFORMATION: X IS ANY ONE AMINO ACID

<400> SEQUENCE: 6

Xaa Thr Ala Thr Ile Ser Ser Tyr Ser Asp Val Ala Thr Ala Val Ser
1               5                   10                  15

Ser Lys Xaa Ser Thr Val
            20
```

COPPER TOLERANT YEAST AND PECTINASES PRODUCED BY THE YEAST

BACKGROUND OF THE INVENTION

The present invention relates to a copper tolerant yeast, the use of the yeast to recover copper from a solution and a pectinase produce by the yeast and the use of the pectinase.

The present invention also relates to a method of hydrolyzing pectins contained in the pectin-containing substrates. The present invention also relates to a method of producing galacturonate.

The influences of mine-pollution have been argued since the damages caused by the mine-pollution were spread out because of the wastewater flew into rivers. The damages include Ashio copper mine pollution injury (about 1980), Minamata disease caused by methyl mercury (1950's) and Itai-Itai disease (about 1940). However, it is not well known how the heavy metals affect organisms at the cellular levels. Those firstly affected by heavy metals under the natural environment are microorganisms. Many heavy metal tolerant strains are obtained to reveal the influence of heavy metals on organisms and to depollute the polluted area of rivers or lands. Many of these strains were bacterial strains.

Among the heavy metal tolerance, many reports have been published about copper tolerant microorganisms and their copper tolerance. For *Escherichia coli*, some plasmids are involved in copper tolerance by reducing Cu(+2) to Cu(+1) (Brown et al., 1992). A copper tolerant strain has also been obtained for budding yeast *S. cerevisiae*, wherein the strain acquired the copper tolerance to about 1 mM copper by detoxicating Cu(+2) to insoluble CuS by producing large amount of $H_2S$ (Ashida, 1965). Thus, the mechanisms known in the prior art are based on the reduction of Cu(+2) to Cu(+1) after incorporating copper ion into cells. Many of these investigations are carried out on bacteria, and indeed, many microorganisms which have been utilized are bacteria. The foregoing report for *S. cerevisiae* is one of the limited examples of these investigations on eukaryotes.

Yeast is the representative example of eukaryotes, and is an important microorganism for investigating the influences of heavy metals on human beings which is another representative example of eukaryotes. The sources for isolating yeasts are widely spread, including the surfaces or internals of animals or plants, soils, atmosphere and rivers. Although there are few examples where yeasts were isolated from deep-sea, yeasts were isolated from deep-sea sediments collected by manned submersibles "SHINKAI 2000" and "SHINKAI 6500". To date, 24 of deep-sea yeast strains were also isolated from deep-see sediments of Sagami Bay (1100-1400 m depth) and 13 strains were isolated from Japan Trench(4500-6500 m depth). The features of yeasts living in such a special environment have not been sufficiently revealed, because it has been difficult to obtain such yeasts themselves. Furthermore, it has been unknown about what kind of enzymes such yeast may secrete.

Generally, many applications of enzymes are known in the fields of foods or cosmetics. Especially, in the field of food industry, pectinases, polygalacturonases and pectin liases, which hydrolyze pectins, have been used for producing clear fruit juice or as a tool for removing endocarps of citruses. Pectin is an acidic polysaccharide which is unique to the non-lignified tissues and is known to be present in the peel of citrus fruits or fruits such as apple and constitutes the cell walls or intercellular substances in the form associated with galactan or arabinan. In the field of food industry where fruits are use as materials, a large amount of peels removed to obtain pulps should be discarded, which raised some problems from the viewpoint of cost for processing them and the effective utilization of resources. Furthermore, the effective utilization of resources is also desired because galacturonate, which is the hydrolyzed product of pectin, may be used during food processing as an acidifier and it is notable as diet foods because of their low calorie. It can be also noted that the effective utilization of resources has been insufficient in that vitamins are discarded with peels, although peels contain larger amount of vitamins than pulps in general. Therefore, a method for efficiently decomposing pectins has been desired. Especially, pectinases having high activity under wide range of conditions and methods for providing such pectinases in large scale have been strongly desired.

There have been several reports on yeast pectinases. For examples, the pectinase secreted by budding yeast *Saccharomyces cerevisiae* is known to have the optimum pH of 5.5 and the optimum temperature of 45° C. (Blanco, et al., 1994). On the other hand, there are fewer reports for pectinases secreted by *Cryptococcus albidus*. Brown et al. (1985) describes that the pectinase secreted by *Cry. albidus* had a molecular weight of 41,000 and had the optimum pH of 3.7 and optimum temperature of 37° C. Previously known pectinases loose almost all the activities in the presence of $Hg^{2+}$, $Cu^{2+}$, $Fe^{2+}$, and $Al^{3+}$ due to the denaturation of proteins However, there have been no reports on whether the pectin hydrolyzing enzymes are produced and secreted by such deep-sea yeasts and there have been also no reports on the physiochemical and biochemical characteristics of such enzymes.

SUMMARY OF THE INVENTION

The object of the present invention is to provide a yeast which is tolerant to copper and has the ability to incorporate copper at a high concentration.

Further object of the present invention is to provide a method of removing copper from extracellular solution or recovering copper from external solution.

Another object of the present invention is to provide a copper tolerant pectinase.

Another object of the present invention is to provide a pectinase having high activity even at high temperature.

Further object of the present invention is to provide a method of effectively hydrolyzing a peel of fruit.

Another object of the present invention is to provide a method of producing galacturonate or vitamins.

The present invention includes a yeast which is tolerant to copper, a pectinase produced by the yeast, a method to produce the pectinase, a method of hydrolyzing pectin-containing materials.

Particularly, the present invention includes a copper tolerant yeast *Cryptococcus* sp. N6 strain isolated from deep-sea sediments and pectinases produced by the yeast.

The yeast of the present invention, *Cryptococcus* sp. N6 strain, has been deposited to the National Institute of Bioscience and Human-Technology Agency of Industrial Science and Technology (currently, National Institute of Advanced Industrial Science and Technology) Ministry of International Trade and Industry (1-3 Higashi 1 chome Tsukuba-shi Ibaraki-ken 305-8566, Japan) under the deposit number of FERM BP-6998 on Jan. 14, 2000.

BRIEF DESCRIPTION OF THE DRAWINGS

FIG. 1 is the graph illustrating the growing manner of N6 strain under copper ion. In the figure, the longitudinal axis indicates the cell number per unit volume (cells/ml) and the horizontal axis indicates the time (hour) after adding $CuCl_2$. □: 0 mM; □: 1 mM; □: 10 mM; □: 20 mM.

FIG. 2 is the graph showing the survival rate calculated from the number of colonies appearing after culturing *Cryptococcus* sp. N6 or *Cryptococcus albidus* IFO-0378 strain in a liquid medium in the presence of $CuSO_4$ and plating predetermined number of each microorganism on YPD agar medium. FIG. 2A shows the survival rate of *Cryptococcus* sp. N6 and FIG. 2B shows the survival rate of *Cryptococcus* IFO-0378. □: 0 mM; □: 1 mM; □: 10 mM; □: 25 mM.

FIG. 5A is the graph showing the absorbance at 280 nm, $A_{280}$ and FIG. 5B is the graph showing the pectinase activity in the fractions in the proximities of the peak. In each graph, the horizontal axis indicates the tube number used for fractionation.

FIG. 11 the comparison of N-terminal amino acid sequences of p36 or p40 with those of known proteins. In the Figure, "A" represents the 22 amino acids N-terminal sequence of p36 and p40 (SEQ ID NO: 6, and "B" represents the amino acid sequence of endopolygalacturonase (pgA) from Fusarium moniliforme (SEQ ID NO: 7).

DESCRIPTION OF THE PREFERRED EMBODIMENTS

Figure 3:
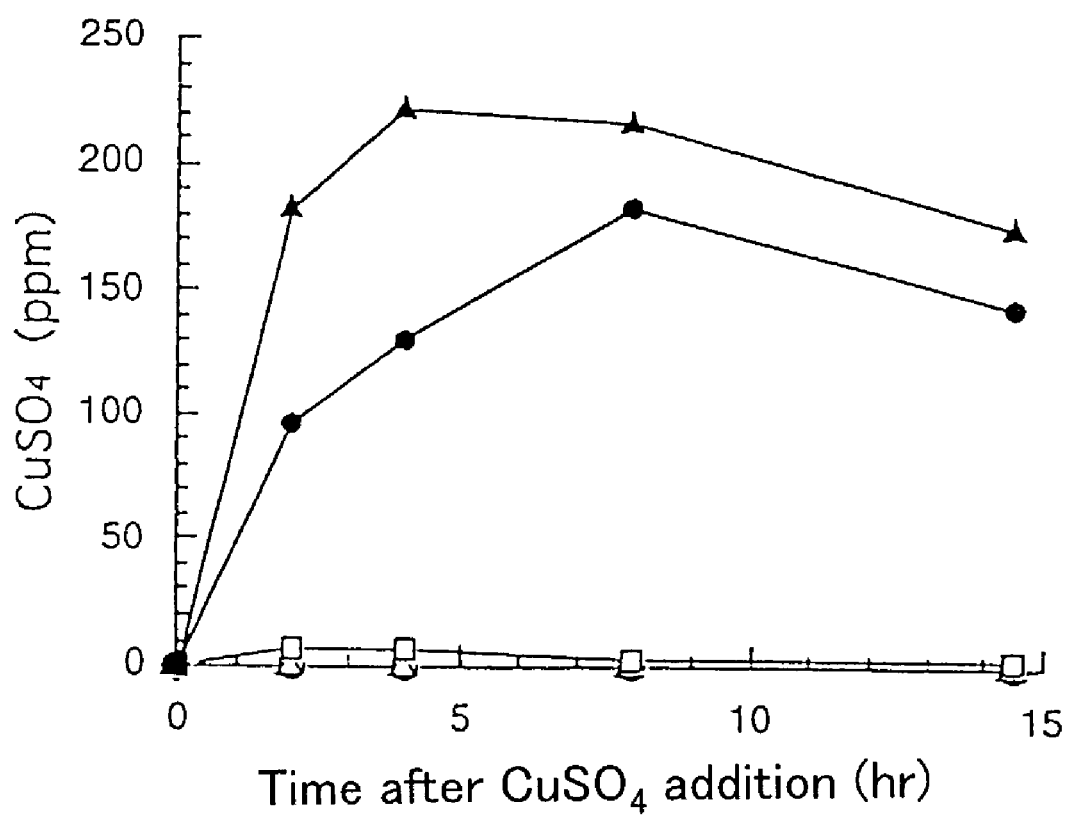
FIG. 3 is the graph showing the time course of the concentration of copper in the cells of *Cryptococcus* sp. N6 strain after adding $CUSO_4$. In the Figure, "□" represents no $CuSO_4$, "□" represents 1 mM $CuSO_4$, "□" represents 10 mM $CuSO_4$, "□" represents 20 mM $CuSO_4$, and "□" represents 50 mM of the concentration of outer solution, respectively. The longitudinal axis indicates inter-cellular copper concentration (ppm).

In the present invention, yeasts are firstly isolated from deep-sea sediments using an appropriate medium and a selection method. It is generally important in investigating a particular new microorganism to select a strain which is used as a reference to be compared. Thus, the genius of the yeast is firstly defined in the present invention. The reference strain is then selected based on the obtained knowledge and the copper tolerance and the ability of copper incorporation will be estimated. Then, the pectinase secreted by the yeast is isolated and its physiochemical and biochemical properties are determined. The yeast of the present invention, FERM BP-6998, may also be referred to as *Cryptococcus* sp. N6 strain or simply N6 strain hereinafter.

The deep-sea yeast of the present invention can be isolated by using an appropriate medium and an appropriate culture condition. A conventional medium and conditions can be used which are well known to those skilled in the art. During this process, any known methods to remove the contamination of other microorganism including fungi may be additionally used. Thus isolated deep-sea yeasts may be classified by the methods usually used for the classification of microorganisms using, for example, the shape of colonies, assimilation of sugars, fermentative ability, nitrate assimilation, requirement for vitamins, or production of carotenoids as criterions. More specific determination of the genus may be preferably performed by, for example, the nucleotide sequence of 18S rDNA.

The effects of heavy metals on the growth and the viability of the isolated deep-sea yeasts are then determined. The heavy metals are supplied to the medium as ions, particularly as a sulfate, a chloride and the like. For example, copper may be supplied as copper sulfate ($CuSO_4$) or copper chloride ($CuCl_2$). Yeasts grown up to the log phase are cultured in such a medium for predetermined periods and the number of cells is determined. The cell number is preferably calculated using hemocytometer but any other method can be used. The viability may be calculated by counting the number of appeared colonies, after transferring the yeasts which has been grown up to log phase into the medium containing a heavy metal and incubating for a predetermined period and then allowing to grow in the growth medium. The calculation formula is as follows:

Viability CFU(%)=(number of appeared colonies)/ (number of plated cells on the YPD agar plate)×100

Alternately, yeasts were stabbed on agar plates containing a heavy metal, and then the size of colonies obtained after a predetermined incubation period is compared each other.

in the culture of the yeast of the present invention, the temperature is similar to that used for normal yeasts, which is preferably about 15° C. to about 26° C., more preferably about 24° C. to 26° C., but the yeast can be also cultured at the temperature as low as about 1° C. to about 15° C. To confirm the copper tolerance of the yeast of the present invention, the copper concentration in the medium will be preferably about 1 mM to about 10 mM, and the concentration of about 5 mM to about 10 mM is particularly preferable. The yeast of the present invention may be acclimatized to copper ion to obtain copper tolerant yeasts to higher copper concentration. For this purpose, yeasts grow in the medium containing 1 mM of copper ion are selected and transferred to the medium having increasing copper concentration to be acclimatized to copper ion. By this method, yeasts can be obtained which can grow in the medium containing copper ion at the concentration of at least up to 50 mM. It is known that copper ion concentration of 50 mM is toxic.

Additionally, the yeas of the present invention can incorporate copper intracellularly when it is grown in the presence of high copper concentration over 20 mM. To incorporate copper ion into the yeast of the present invention, it is only required to grow the yeast in the environment containing copper at a high concentration. The culture period is at least 30 minutes, usually about 1 to about 15 hours, preferably about 1 to about 8 hours, and about 4 to about 6 hours is particularly preferable. For culture, conventional conditions usually used for the culture of yeast may be used, except for copper ion concentration. For the incorporation of copper by the yeast of the present invention, the copper ion concentration in the external solution is preferably not less than about 20 mM, more preferably, the concentration is about 20 mM to about 50 mM. Culturing the yeast of the present invention under such conditions, copper can be accumulate in the cell or on the cell surface up to about 100 ppm to about 200 ppm. Alternately, the yeast of the present invention may be immortalized on a membrane or a column and a copper containing solution may be passed on the membrane or through the column to accumulate copper in the yeast cell or on the cell surface. The yeast wherein copper is accumulated by such methods may be recovered and crushed in the buffer using the methods known in the art, and then, copper may be recovered by known methods. Buffers and cell crushing methods suitable for such a purpose are well known to those skilled in the art.

To investigate what kind of enzymes the yeast of the present invention secretes, known methods for individual enzyme can be used. Particularly, whether the yeast secretes enzymes having pectinase activity can be determined by testing the formation of halo on the agar medium containing pectins. Using such methods, it is confirmed that the yeast of the present invention produces a pectinase(s). Thus, the pectinases of the present invention can be obtained by culturing the yeast of the present invention and by purify the culture solution. The purification of the pectinases of the present invention can be performed by applying any method conventionally used for pectinase to the culture solution of the yeast of the present invention. Briefly, the pectinases secreted into the culture medium may be purified according to the following process.

The yeast is grown for about 15 hours at about 24° C. in the appropriate medium such as YAP liquid medium and the supernatant is prepared by centrifuging the medium for about 5 minutes (8000 rpm). The supernatant is subjected to the ammonium sulfate precipitation method, which is the method usually used for fractionation of proteins. Each fraction obtained by ammonium sulfate precipitation is examined for the pectinase activity using the following measuring method. The fractions having pectinase activity are then washed with ammonium sulfate solution of corresponding concentration, dissolved in an appropriate buffer such as 10 mM acetate buffer (pH5.0) and demineralized over night. Demineralization is preferably performed by gel filtration or by dialysis. The fractions are then subjected to cation exchange chromatography to obtain the fraction containing only a single protein species. Any method known in the art can be used to determine the molecular weight, such as SDS-polyacrylamide electrophoresis (SDS-PAGE). Thus purified pectinases may be directly used or stored at a low temperature, or may be concentrated before use or storage. To concentrate each sample, commercially available ultra centrifuge filtration units such as membrane attached Ultrafree 15 Unit from Millipore can be used. Additionally, the obtained pectinases can be lyophilized and stored.

The pectinase activity of the pectinase is determined by using the following method. The activity of the pectinase can be determined by conventional methods used for this enzyme, such as galacturonate quantitative measurement described by Gross et. al.(Gross, K. C., Hort Science, 17, 933-934, 1982). Briefly, the yeast are cultured in YAP liquid medium at 24° C. for about 15 hours and the culture supernatant is used as a starting material for pectinase purification. It is preferable to use polygalacturonate (Sigma, P-3889, Rot No.106H10004) which has been washed with 80% ethanol as a substrate for the determination of enzyme activity, because pectin preparations contain impurities. In the polygalacturonate solution of predetermined concentration such as about 0.2% in 0.2M acetate buffer (pH5.0), ⅑ volume of a sample is added and reacted at 24° C. for 1-3 hours. To ⅒ volume of the reaction product, 5-fold volume of ice cold 100 mM borate buffer (pH9.0) was added followed by adding equal volume of 0.2% solution of 2-Cynamoacetamide (Wako, 030-04942, Rot No. PAQ1877), boiling at 100° C. for 10 minutes and measuring the absorbance at 276 nm ($A_{276}$). Alternately, to a defined volume of the reaction product 3 volumes of 3,5-dinitro salicylic acid (DNS) reagent is added and the absorbance at 500 nm ($A_{500}$) is measured after heating at 100° C. for 10 minutes (DNS method) (Summer, 1921; Hostettler et al., 1951; Borel et al., 1952). The activity is represented as 1 unit (1 U) when the absorbance at 276 nm (A276) is changed by one in 1 minute and 1 mU is defined as ¹⁄₁₀₀₀ of 1 U. Alternately, the activity is indicated as a relative percentage of the activity based on the highest activity in each measurement as 100%. The specific activity is defined as a unit number per 1 μg of the protein.

Once the purified pectinase is obtained, then the amino acid sequence thereof is analyzed. The amino acid sequence may be determined by conventional methods known in the art, for example by using commercially available amino acid auto-sequencer. The pectinases of the present invention may be used for hydrolyzing pectins in the same manner as the normal pectinases but also may be used under more wide-ranging condition, for example, at a temperature as low as about 20° C. or in the presence of about 10 mM copper ion, because they has the activities under copper ion environment or at a temperature different from those for ordinary pectinases. Particularly, the pectinases of the present invention remain active over wide ranging temperature extending from as low as about 0° C. to as high as about 70° C., and thus, it can be used in various environments. Specifically, the pectinases of the present invention can function at pH 4-6 and at the temperature of 0° C.-60° C.

Particularly, the pectinase of the present invention having the molecular weight of about 36 k may function at a temperature of about 0° C. to about 50° C., preferably about 10° C. to about 60° C., more preferably about 20° C. to about 40° C. and most preferably about 30° C. to about 40° C. The pectinase of the present invention having the molecular weight of about 40 k may function at a temperature of about 0° C. to 40° C., preferably about 10° C. to about 50° C., more preferably about 10° C. to about 40° C., and most preferably about 30° C. to about 50° C. However, both of the two pectinases of the present invention can be used at a temperature of 0° C. to 20° C., because both of them have relatively high activity even at a low temperature. Thus, the two pectinases can be selectively used according to the purposes or the environments.

The pectinases of the present invention can be used for hydrolyzing pectin-containing materials such as peels of fruits. For this purpose, the purified or partially purified pectinases of the present invention may be added directly to pectin-containing materials such as peels of fruits, but also more conveniently, the yeast or the present invention secreting the pectinases may be co-cultured with pectin-containing materials such as peels of fruits, or the culture supernatant of the yeast of the present invention may be contacted with pectin-containing materials directly and/or after concentration. Optionally, pectin-containing materials such as peels of fruits may be sterilized to suppress the growth of bacteria. The sterilization may be generally conducted by high temperature sterilization but any other methods can be used provided that the methods do not inhibit pectinase activity. The conditions for the pectinase of the present invention to function may be selected from the foregoing range where the pectinases can retain their activities, for example, a temperature of about 0° C. to about 60° C. and a pH range of 4 to 6 may be adopted.

These conditions may be selected depending on the nature of pectin-containing materials and the purpose of hydrolyzing. However, when the yeast of the present invention is directly used as a source of the pectinases of the present invention, it is preferable that the conditions may be those under which the yeast can propagate. For example, the temperature range may range from room temperature to about 37° C. By using such methods, pectin-containing materials such as peels of fruits can be easily and conveniently hydrolyzed and the galacturonate containing hydrolysates, which are the results of the hydrolyzation of pectins, may be also obtained. When peels of fruits are use as pectin-containing materials, hydrolysates containing galacturonate and various vitamins may be obtained. These hydrolysates are processed using the methods well known to those skilled in the art to recover galacturonate and vitamins from the processed hydrolysates, after removing solid components.

EXAMPLES

Example 1

Identification of Deep-sea Yeast (1) Taxonomy

N6 strain was investigated for sugar assimilation, fermentative ability and nitrate assimilation. The results are shown in Table 1.

TABLE 1

The characteristics of N6 strain

Shape : Spherical
Assimilative ability for sugars:
   G  Ra  Er  Su  St  Ri  Ma  Xy  Mn  Ce  Ar  Sa  Tr  Ri  Ca  La  Rh  I  Mz  Me
   +   +   −   +   +   +   +   +   +   +   +   −   +   +   −   +   +   +   +   +
Fermentative ability:
   G  Ga  Ra  Ma  Su  Tr  La
   −

Assimilative ability for nitrate: +
Urease: −
Vitamin requirements: +
Carotenoid Production: +
Amylolysis: −
DNase Production: −

G: galactose,
Ra: Rafinose,
Er: Erythritol,
Su: Sucrose,
St: Solubilized starch,
Ri: Ribitol,
Ma: Maltose,
Xy: D-Xylose,
Mn: D-Mannitol,
Ce: Cellobiose,
Ar: L-arabinose,
Sa: Succinic acid,
Tr: Trehalose,
Ri: D-Ribose,
Ca: Citric acid,
La: Lactose,
Rh: L-Rhamnose,
I: Inositol,
Mz: Melezitose,
Me: melibiose (2) Determination of 18S rDNA Partial Nucleotide Sequence A small amount of *Cryptococcus* sp. grown on YM (0.5% Bacto peptone, 0.3% Bacto yeast extract, 0.3% malt extract, 1.0% glucose) agar plate was picked up by an aze, suspended in 200 μl of Extraction buffer (50 mM Tris-HCl (pH7.5), 50 mM EDTA, 3% SDS) and crushed on an ice bath with microprestel after adding one aze of aluminum oxide. To the sample 100 μl of TE (50 mM Tris-HCl (pH8.5), 1 mM EDTA)-saturated phenol and 100 μl of chloroform were added, and then vigorously agitated for 1 minute followed by centrifugation (1200 rpm) for 1 minute (phenol-chloroform extraction). To the supernatant, 100 μl of chloroform was added, and vigorously agitated for 1 minute followed by centrifugation (1200 rpm) for 1 minute to obtain the supernatant (chloroform extraction). To the supernatant 20 μl of 3M sodium acetate (pH5.2) and 200 μl of isopropanol were added and cooled to −20° C. for 10 minutes followed by centrifugation for 20 minutes (1200 rpm), and the supernatant was discarded (isopropanol precipitation). The remained precipitant was washed and desalted by 70% ethanol, dried in a vacuum centrifugal dryer for 10 minutes and dissolved in 200 μl of TE. To the solution, 10 μl of RNase (RNase A 80 mg/ml, RNase T1 50 units/ml) was added and reaction was carried out at 37° C. for 1 hour. For the solution, phenol/chloroform extraction and chloroform extraction were conducted for once respectively and subjected to isopropanol precipitation. The precipitant was used as the template DNA for PCR.

PCR was performed using NS1 (gTA gTC ATA TgC TTg TCT C)(SEQ ID NO: 1) and NS8 (TCC gCA ggT TCA CCT ACg gA) (SEQ ID NO: 2) as primers and the DNA as a template with Ex Taq Kits (Takara) (94° C., 2 min.→(94° C., 1 min→58° C., 1 min.→72° C., 2 min)×30 cycles). Next, PCR was performed using NS1 (gTA gTC ATA TgC TTg TCT C), NS2 (ggC TgC Tgg CAC CAg ACT TgC) (SEQ ID NO: 3), NS3 (gCA AgT CTg gTg CCA gCA gCC) (SEQ ID NO: 4) and NS7 (gAg gCA ATA ACA ggT CTg TgA TgC) (SEQ ID NO: 5) as primers with SewuiTherm Long Read Sequencing (EPICENTER TECHNOLOGIES) Kits. The condition of the PCR was 95° C., 2 min., followed by 30 cycles of 95° C., 30 sec., 50° C., 15 sec., 70° C., 15 sec, and cooled to 4° C. The partial sequence of 18S rDNA was thus determined and the sequence was compared with the sequences of known species in the database.

The analysis of 18S rDNA sequence of N6 strain showed 98.6% homology to the sequence of *Cryptococcus albidus*. Consequently, N6 strain was classified as a basidiomycete belonging to *Cryptococcus*, and therefore, *Cryptococcus albidus* type strain, IFO 0378 was selected as a reference strain.

<Sequence Listing Free Text>
SEQ ID NO: 1-6: PCR primers for amplification of 18S rDNA partial sequence.

Example 2

Effects of Copper Ion on the Growth (1) Effects of Copper Ion on the Growth Curve To each of the cultures of N6 strain or *Cry. albidus* IFO 0378 grown to mid log phase ($1.0 \times 10^7$ cells/ml) in YPD (1.0% Bacto Yeast Extract, 2.0% Bacto Peptone, 2.0% Glucose) liquid medium copper chloride ($CuCl_2$) or copper sulphate ($CuSO_4$) was added at a final concentration of 0, 1, 10 or 20 mM and the strains were further cultured at 24° C. The cell number was determined at 2, 4, 8 and 10 hours after adding copper using a hemocytometer. The results showed that N6 strain grew in the YPD medium containing $CuCl_2$ or $CuSO_4$ at the final concentration of 1-10 mM to the similar extent as in normal YPD medium (FIG. 1A). On the other hand, *Cry. albidus* IFO 0378 gradually decreased its grow rate after 2 hours when $CuCl_2$ or $CuSO_4$ was added at a concentration of 1 mM and could not grow at a concentration of 10 mM (FIG. 1B).

(2) Enhancement of Copper Tolerance by Acclimatization

N6 strain was shown to be able to grow in a medium containing up to 10 mM of $CuSO_4$, as described above. The extent to which the $CuSO_4$ tolerance of N6 strain can be enhanced by acclimatization was investigated. Acclimatization culture was carried out on YPD agar medium at 26° C. by transferring the yeast grown on the medium containing 1 mM $CuSO_4$ to the medium containing 5 mM of $CuSO_4$. The results showed that the growth rate of the yeast was comparative to the growth rate on the normal YPD agar medium when the $CuSO_4$ concentration was 1-20 mM. The growth rate decreased gradually when $CuSO_4$ concentration was more than 20 mM, but it was finally demonstrated that the yeast could still growth on the medium containing up to 50 mM $CuSO_4$. During the growth, it was observed that the color of colonies gradually changed from original yellowish white to pale blue which is the color of hydrated copper ion.

On the other hand, *Cry. albidus* IFO 0378, *Saccharomyces cerevisiae* IFO2374 (sake yeast) or typical deep-sea yeast *Rh. ingeniosa* IFO10002 decreased their growth rate on the YPD agar medium containing $CuSO_4$ at a concentration of 1 mM and could hardly grow when the concentration was 5 mM. These results are summarized in Table 2. The similar results were obtained when $CuCl_2$ was used.

TABLE 2

Increase in copper tolerance by acclimatation

| | $CuSO_4$ final concentration (mM) | | | | | | | |
|---|---|---|---|---|---|---|---|---|
| Strain | 0 | 1 | 5 | 10 | 20 | 30 | 40 | 50 |
| *Cryptococcus sp.* N6 (deep-sea yeast) | +++ | +++ | +++ | +++ | +++ | ++ | ++ | + |
| *Cryptococcus albidus* IFO-0378 | +++ | ++ | + | − | − | − | − | − |
| *Rhodotorula ingeniosa* IFO-10002 | +++ | ++ | − | − | − | − | − | − |
| *Saccharomyces cerevisiae* IFO-2347 | +++ | ++ | − | − | − | − | − | − |

+++: vigorous growth,
++: medium growth,
+: possible to grow,
−: no growth

Example 3

Effects of Copper Ion on the Viability

To the culture of N6 strain and *Cry. albidus* IFO0378 grown in the YPD liquid medium up to the mid log phase ($1.0 \times 10^7$ cells/ml) $CuCl_2$ or $CuSO_4$ was added at a final concentration of 0, 1, 20 and 20 mM, respectively, and were cultured at 24° C. After 2, 4, 8 and 10 hours, the cultures were streaked on YPD agar medium and incubated at 26° C. for 2 days. The viability was calculated based on the appeared colonies.

The results showed that N6 strain was 100% viable in the YPD liquid medium containing 1 mM $CuSO_4$. The results also showed that the viability decreased up to 10 hours later after 10 mM $CuSO_4$ was added to the culture (FIG. 2A) but viable cells gradually increased later. On the other hand, the viability of *Cry. albidus* IFO 0378 significantly decreased even after 1 mM $CuSO_4$ was added, and the microorganisms completely died after 25 hours in the presence of 10 mM $CuSO_4$ (FIG. 2B). Additionally, by harvesting and observing N6 strain and *Cry. albidus* IFO 0378 cells, it was shown that the viable cells were white but the dead cell became pale blue. Similar results were obtained when $CuCl_2$ was used.

Example 4

Determination of Intercellular Copper Concentration

N6 strain in the mid log phase was cultured with $CuSO_4$ addition, and the intercellular copper was determined using atomic absorption spectrum method after predetermined period of cultivation. The results are shown in FIG. 3. Copper was scarcely detected in cells when the medium was not supplemented with $CuSO_4$ and the intercellular copper concentration was as low as 7 ppm per $10^8$ cells when the concentration of $CuSO_4$ was below 10 ppm. On the contrary, the intracellular copper concentration was significantly as high as 150-200 ppm or more per $10^8$ cells when the concentration of $CuSO_4$ in the culture medium was 20 mM-50 mM. The intracellular copper accumulation was observed at 30 minutes or later after adding $CuSO_4$, increased up to about 5-8 hours, and then, the accumulation slightly decreased (FIG. 3).

Example 5

Analysis of Other Characteristics

Analysis of the fatty acid composition of cells revealed that C18:3 (linolenic acid) increased with the decrease of C18:1 (oleic acid), after 10 mM $CuSO_4$ was added.

On the other hand, the differences in the electrophoresis pattern of cellular proteins caused by the presence or absence of copper ion in the culture were not observed. Additionally, N6 strain was shown to be tolerant against ultrasonication or heat treatment and was not destroyed, probably because the cell wall of N6 strain is stronger than Cry. albidus IFO 3078. Analysis of sugars contained in the outer surface suggested that the main component was a neutral sugar, but the significant difference between N6 strain and Cry. albidus IFO0378 was not observed.

Example 6

Identification of Halo Formation

N6 strain and Cry. albidus IFO0378 were stubbed respectively on YPP (1.0% Bacto Yeast Extract, 2.0% Bacto Peptone, 1.0% pectin) agar plates, YAP (0.1% $(NH_4)_2SO_4$, 0.2% $KH_2PO_4$, 0.09% $Na_2HPO_4.H_2O$, 0.1% $MgSO_4.7H_2O$, 0.1% Bacto Yeast Extract, 1.0% pectin) agar plates and SDP (0.67% Yeast nitrogen basic medium, 1.0% pectin) agar plates, and then the formation of halo was investigated after culturing at 26° C. for 4 days. Similar experiments were carried out by using YPP agar medium, YPP agar medium and SDP agar medium where each of them contained 10 mM $CuSO_4$.

The results showed that halos were observed around the colonies on the SDP agar plate. Additionally, N6 strain was stubbed on agar plates containing 10 mM of $CuSO_4$ and was cultivated at 26° C. for 2 days. Halos were observed around the colonies only when YPP agar plates were used. On the contrary, Cry. albidus formed neither colony nor halo. It was expected that N6 strain secreted a pectinase extracellularly, since a halo was formed. Particularly, the fact that the halo was observed even in the presence of 10 mM $CuSO_4$ indicated that this pectinase had the enzymatic activity even in the presence of copper ion.

Example 7

Detection of Pectinase Activity

N6 strain was culture in liquid YAP medium at 24° C. for 15 hours. The supernatant of the culture was used for the starting materials for pectinase purification. The sample obtained at each step of the purification was examined for pectinase activity according to the following method of quantifying galacturonate (Gross, 1982). In this connection, since a pectin preparation contains many impurities, polygalacturonate (Sigma, P-3889, Rot. No. 106H1004) was used as a substrate after washing by 80% ethanol. 100 µl of sample was added to 900 µl of 0.2% polygalacturonate dissolved in 0.2M acetate buffer (pH 5.0) and the reaction was carried out at 24° C. for 1-3 hours. To 100 µl of the reaction product, 500 µl of ice cold 100 mM borate buffer (pH 9.0) was added, followed by adding 100 µl of 0.2% 2-cyanoacetamide (Wako, 030-04942, Rot No. PAQ1877) solution, heating the reaction product to 100° C. for 10 minutes and the absorbance at 276 nm ($A_{276}$) was determined.

Figure 4:
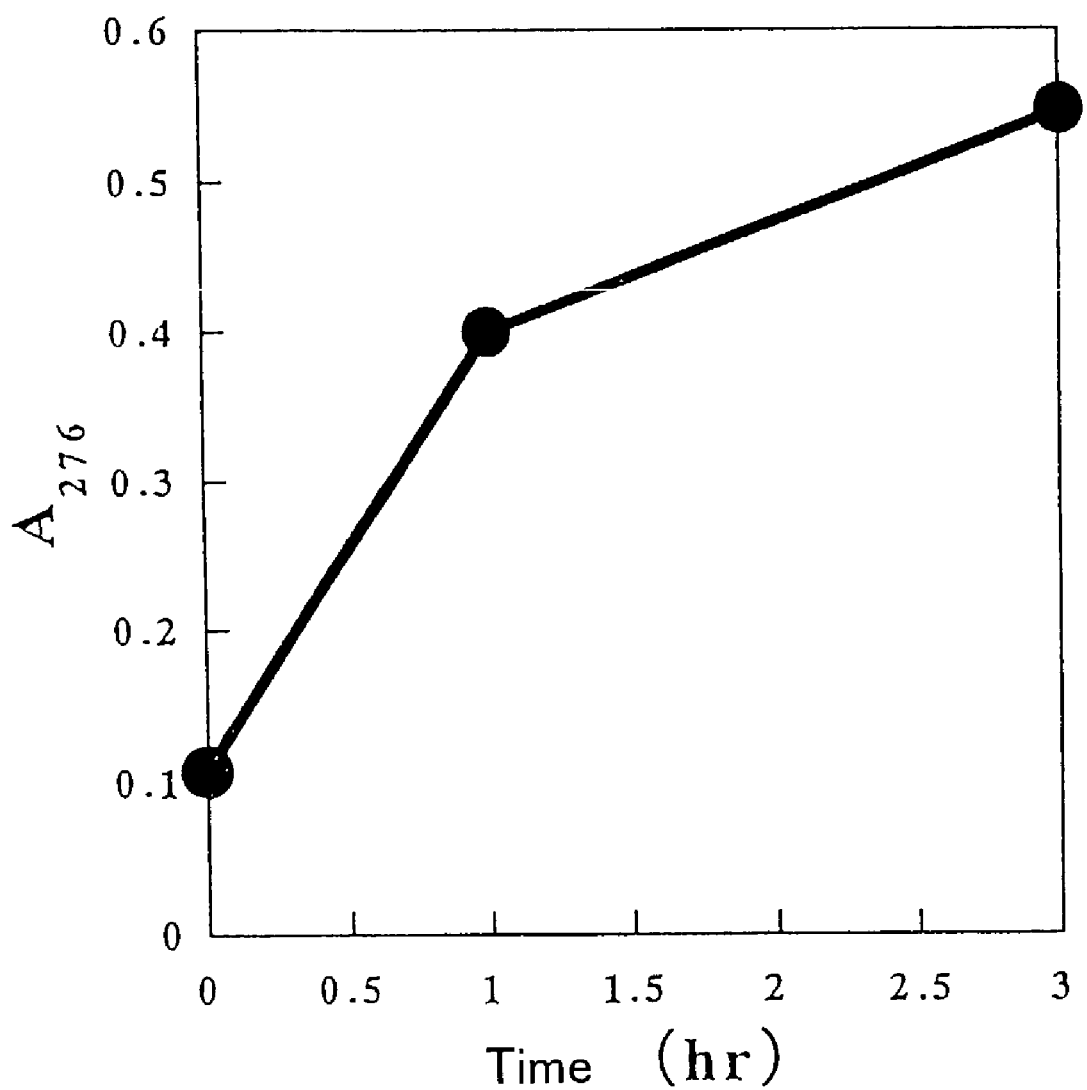
FIG. 4 shows the pectinase activity in the supernatant of the YAP culture of *Cryptococcus* sp. N6 strain. The horizontal axis indicates the culture time (hr) and the longitudinal axis indicate the absorbance at 276 nm.

The results showed that polygalacturonate was apparently degraded with time (FIG. 4). Then, the supernatant was subjected to a heat treatment and then the activity for degrading pectin was determined (Table 3). The results indicated that the factor was actually a protein, because the activity was completely disappeared by treating it at 60-100° C. for 1 hour.

TABLE 3

Inactivation of pectinase activity by heat treatment

| Medium | Temperature for heat treatment (° C.) | $A_{500}$ |
|---|---|---|
| YPP | 24 | 0.148 |
|  | 60 | 0.007 |
|  | 100 | 0.000 |
| YAP | 24 | 0.146 |
|  | 60 | 0.013 |
|  | 100 | 0.000 |

This factor will be referred to "pectinase" and the activity thereof will be referred to "pectinase activity" in the following Examples.

Example 8

Purification of the Pectinases

After culturing N6 strain in YAP liquid medium at 24° C. for 15 hours, the broth was centrifuged for 5 minutes (8000 rpm) to prepare a culture supernatant. The supernatant was supplied for ammonium sulfate precipitation of proteins according to the following procedure. To 3 L of the supernatant 729 g of ammonium sulfate was added, agitated for 30 minutes and centrifuged (8000 rpm) for 15 minutes. The precipitates were discarded, ant 1125 g of ammonium sulfate was further added to the supernatant (final concentration of 90%), agitated for 30 minutes and centrifuged for 15 min (8000 rpm) to recover proteins. The precipitate was washed with 30 ml of 90% aqueous ammonium sulfate solution. dissolved in 50 ml of 10 mM acetate buffer (pH 5.0) and was demineralized by overnight dialysis. Then, it was applied to a cation exchange chromatography by FPLC using CM-TOYOPEARL (TOSOH) to obtain a fraction containing a single protein species. The centrifugal ultrafiltration unit (Membrane equipped Ultrafree 15 Unit 5000, MILLIPORE) was used for concentration of each sample. An aliquot of the sample was removed, to which a sample buffer was added, the solution was heated at 100° C. for 5 minutes and SDS-polyacrylamide gel electrophoresis (SDS-PAGE) was carried out to determine the molecular weight.

To purify the pectinases, ammonium sulfate precipitation was firstly carried out. Using YPP or PAP culture broth, each 100 ml of the culture supernatant ammonium sulfate was added to the final concentration of 30, 50, 70 or 90%, respectively, and the precipitates were recovered, dialyzed followed by the determination of pectinase activity using 0.2% polygalacturonase as a substrate. The results showed that the activity was observed in the fraction precipitated by 50-90% ammonium sulfate precipitation. Thus the proteins precipitated by 40% ammonium sulfate precipitation were discarded and the proteins precipitated at 90% were used for further analysis as an ammonium sulfate fraction sample.

Figure 5:
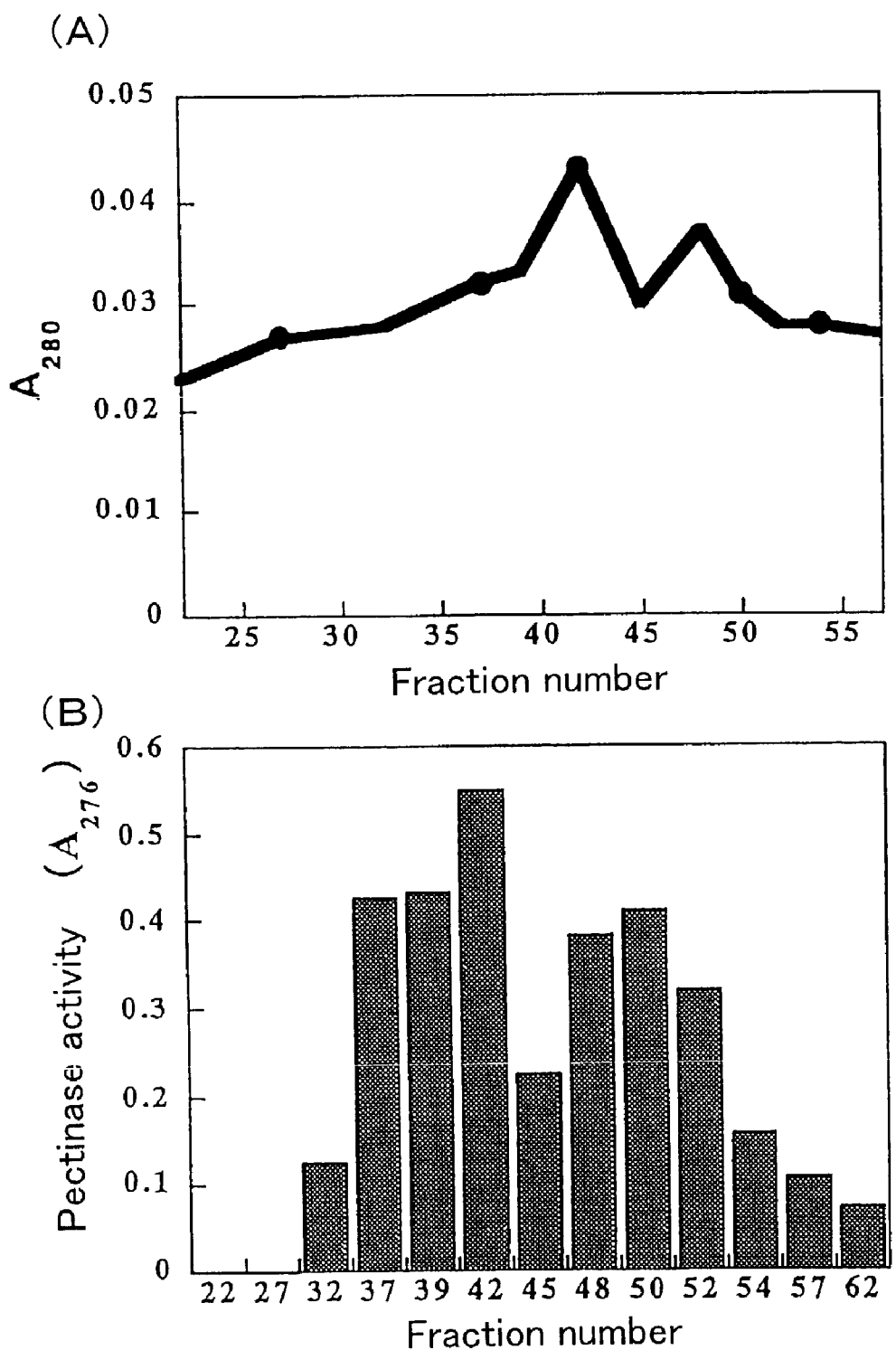
FIG. 5 shows the pectinase activity in each fraction from FPLC and the elution pattern of proteins.

To further precede the purification of the sample obtained by the ammonium sulfate precipitation, chromatography using ion exchange resins was carried out. Firstly, CM-TOYOPEARL and DEAE-Sephadex was used as a cation exchange resin and an anion exchange resin, respectively, and the sample dissolved in 10 mM acetate buffer (pH 5.0) was subjected to the chromatography to determine the activity of the sample which passed through. The results showed that the pectinase activity was adsorbed to the resin when CM-TOYOPEARL was used, but when DEAE-Sephadex was used, the activity was observed in the solution which passed straight through. The results indicated that the interested proteins were adsorbed to CM-TOYOPEARL at pH 5.0. To further separate the proteins improving the purity, a chromatography using FPLC (Pharmacia Biotech) was carried out. 10 mM acetate buffer (pH 5.0), 0.3 M NaCl aqueous solution was used as an elution solution. The chromatography was carried out at a flow rate of 2 ml per 1 min. and the fraction was collected in 2 ml aliquots into tubes. Tow high peaks of proteins caused by the absorption at 280 nm were found in the fraction No. 36 to No. 53 (corresponding to 72-106 ml of elution) (FIG. 5A).

Then, the pectinase activity was examined for this range. It was indicated that the pectinase activity was confirmed as 2 peaks which corresponded well to the peaks of proteins (FIG. 5B). The molecular weight was estimated to be 36,000 and 40,000, respectively as determined by SDS-PAGE. These are herein referred to as p36 and p40, respectively. Then, the increase in the absorption at 235 nm ($A_{235}$) caused by the generation of 4,5-unsaturated galacturonide produced from the degradation of polygalacturonate was determined to confirm that these enzyme were not pectin lyases. $A_{235}$ was determined by adding a sample containing p36 or p40 to 0.2% polygalacturonase as a substrate. The results showed that the increase in $A_{235}$ was not observed even after 1 hour. Thus, these 2 enzymes were actually confirmed to be pectinases.

Example 9

Determination of the Optimum pH and the Optimum Temperature for p36- and p40-pectinase 7 μl of sample was added to 193 μl of 0.1 M acetate buffer (pH 2.0, 3.0, 4.0, 5.0 6.0 or 7.0), 0.1 M HEPES buffers (pH 7.0 or 8.0), respectively, and the reaction was carried out for 10 minutes at 24° C. to determine the pectinase activity. Similarly, 7 μl of sample was added to 0.1 M acetate buffer (pH 5.0) and reacted for 10 minutes at 0, 5, 10, 15, 20, 30, 40, 50 or 60° C. to determine the pectinase activity.

Then, the estimation of the optimum pH and the optimum temperature of these enzymes was carried out. Considering the buffer capacity, 0.1 M acetate buffer was used for pH 2.0 to 7.0 and 0.1 M HEPES buffer was used for pH 7.0 to 8.0. The reaction was carried out at 24° C. for 10 minutes to determine the activity. The results are shown in a graph as the relative enzyme activity percentage based on the maximum enzyme activity in each measurement as 100, after defining the activity as one unit (1 U) if the absorbance at 276 nm ($A_{276}$) changed one (1) per 1 min. In the measurement, the amount of the protein was kept in constant. The amount of the protein was determined by Protein Assay from Bio-Rad.

Figure 6:
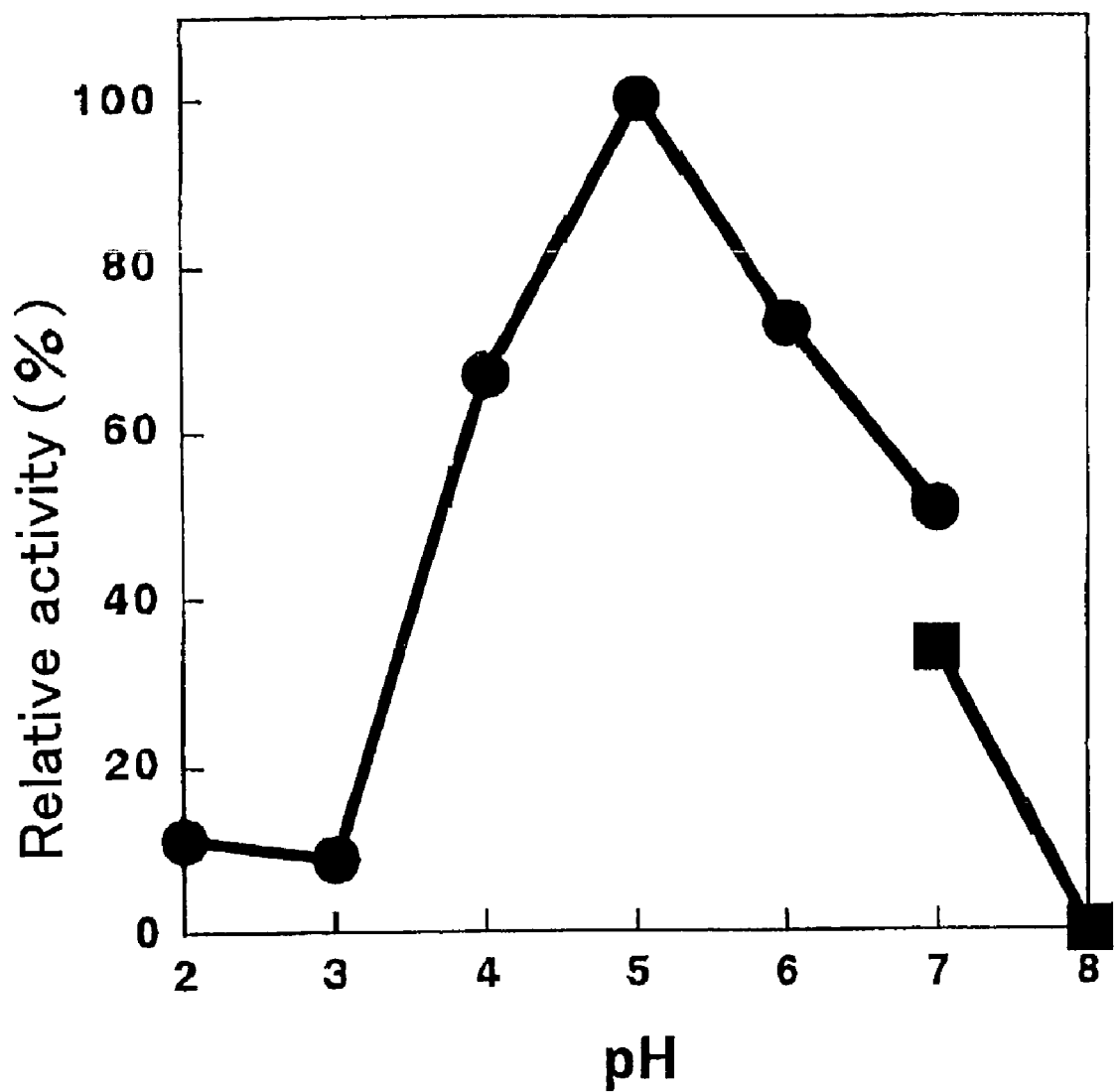
FIG. 6 shows the optimum pH of p36. The determination was carried out in 0.1 M acetate buffer (pH 2.0-7.0: □) or in 0.1 M HEPES buffer (pH 7.0, 8.0: □). The longitudinal axis indicates relative activity where the maximum value is defined as 100.
Figure 7:
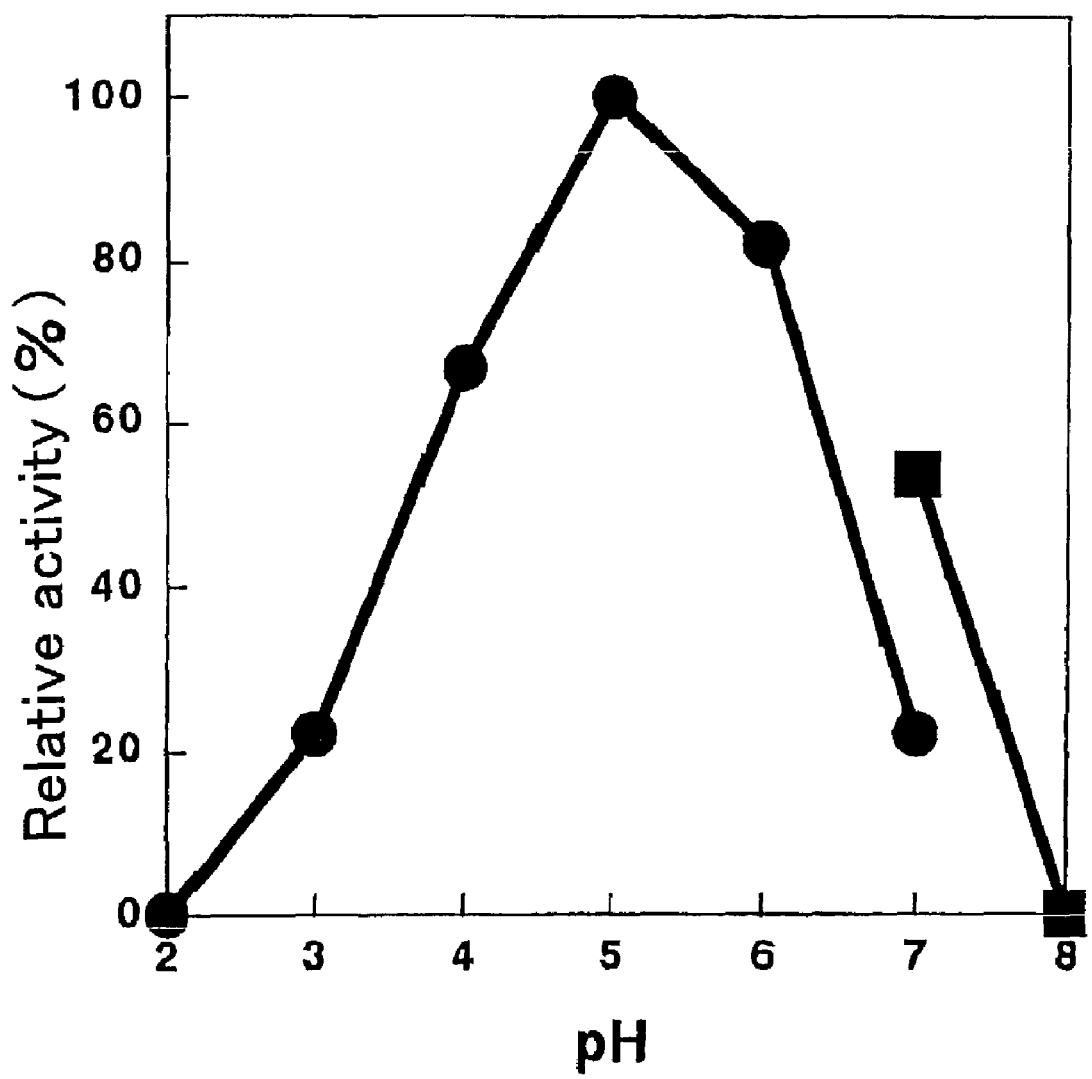
FIG. 7 shows the optimum pH of p40. The determination was carried out in 0.1 M acetate buffer (pH 2.0-7.0: □) or in 0.1 M HEPES buffer (pH 7.0, 8.0: □). The longitudinal axis indicates relative activity where the maximum value is defined as 100.

The results showed that the peak of the activity of p36 was at pH 5.0 and no pectinase activity was observed at pH 2.0-3.0 and pH 8 (FIG. 6). Similar tendency was observed for p40, but it differed from p36 in that t it still had some activity at pH 3.0. Therefore, it was found that both p36 and p40 had the optimum pH of 5.0.

Figure 8:
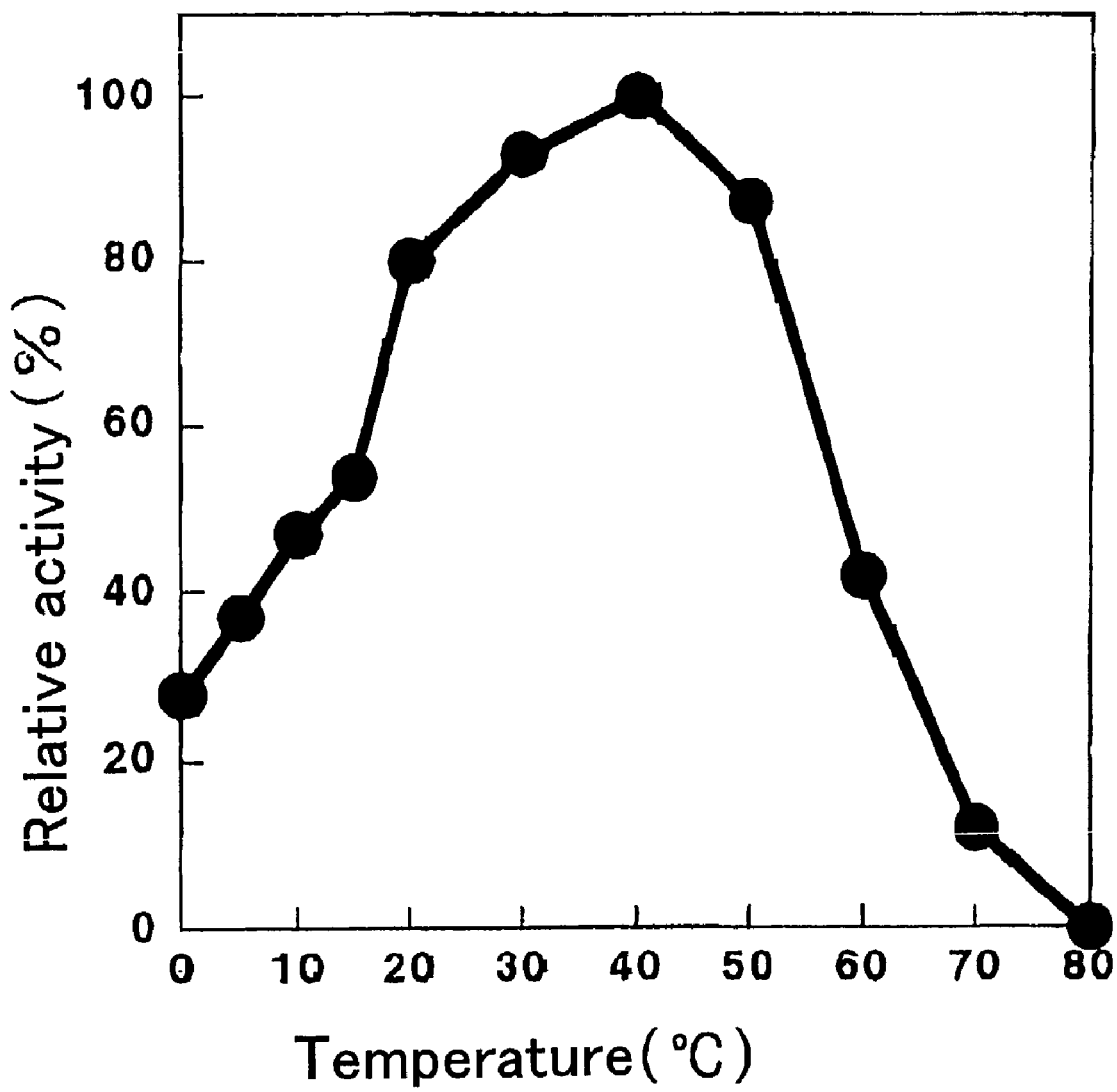
FIG. 8 is the graph showing the optimum temperature of p36. The longitudinal axis indicates relative activity where the maximum value is defined as 100.
Figure 9:
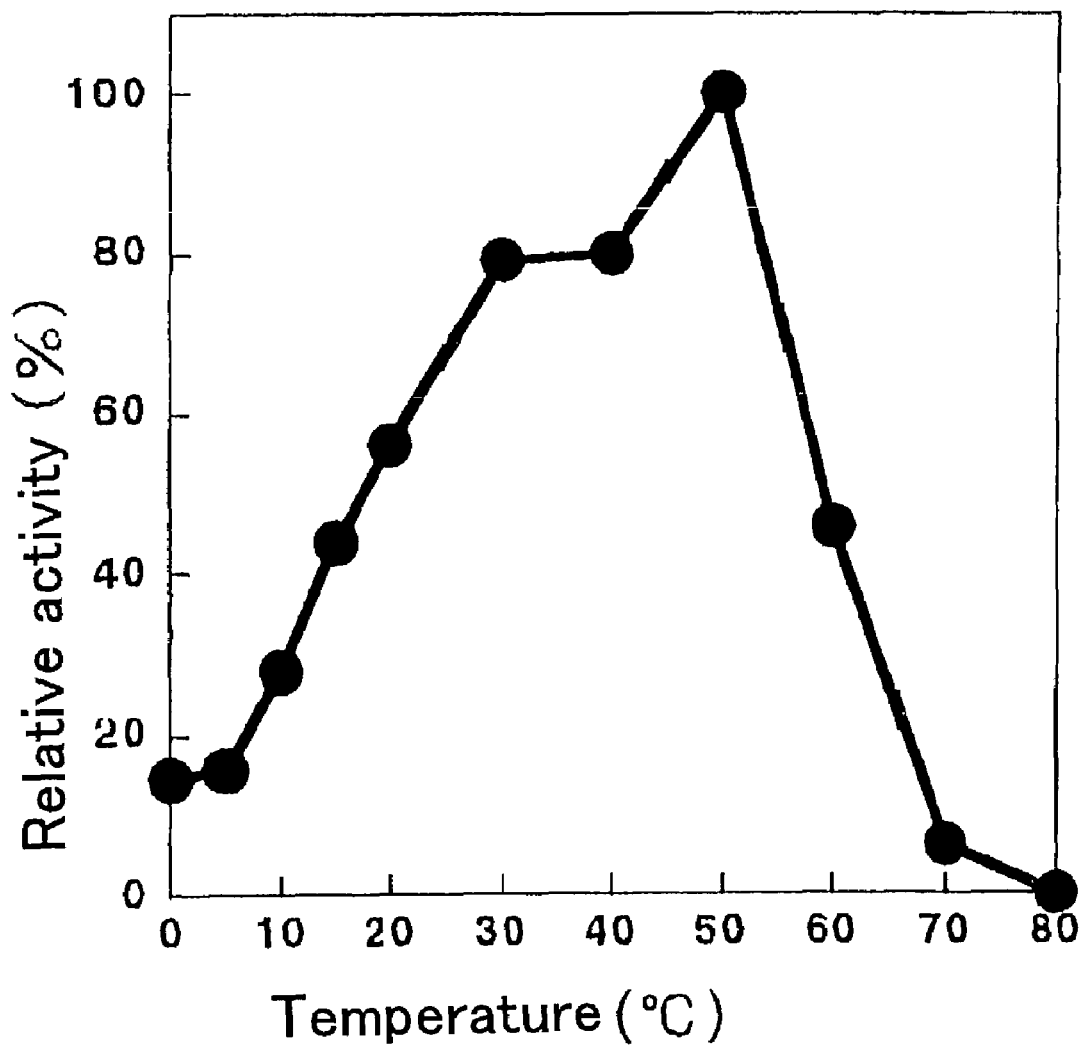
FIG. 9 is the graph showing the optimum temperature of p40. The longitudinal axis indicates relative activity where the maximum value is defined as 100.

Then, the optimum temperature was examined at the optimum pH. The reaction was carried out at 0-60° C. for 10 minutes using 0.1 M acetate buffer (pH 5.0) to determine the activity. The results of the measurement were shown as a graph using relative activity (%) as described above. The results showed that both p36 and p40 exhibited very high enzymatic activity at a temperature as low as 20° C. or less, and that their activities were still observed even at 0° C. and their activities increased gradually up to about 40° C.-50° C. and then decreased (FIGS. 8 and 9). Thus, they had about 40 to 60% of the activity at the optimum temperature respectively and still had about 15-30% activity even at 0° C. (FIGS. 8 and 9). Furthermore, the activity of p40 was highest at 50° C. (FIG. 9). Thus, it was shown that the optimum temperature was 40° C. for p36 and 50° C. for p40.

Example 10

Hydrolysis of the Pericarps of Fruits by the Pectinases Produced by *Cryptococcus* sp. N6 Strain (a) A bunch of mandarin was placed in sterile water and a small amount of *Cryptococcus* sp. N6 strain was inoculated, which were cultured at a room temperature. *Cryptococcus albidus* IFO00378 strain was used as a control, and the similar estimation was carried out for sake yeast, *Saccharomyces cerevisiae* IFO2347 strain.

(b) A bunch of mandarin was placed in the solution which had been concentrated 100-fold by ammonium sulfate precipitation method from the supernatant of the culture where *Cryptococcus* sp. N6 had been grown in YPP medium and was treated at 37° C. As a control, a mandarin was placed in sterile water and similarly examined.

(c) The similar estimation was performed for bunches of mandarin.

The results are shown in Table 4.

TABLE 4

The extent of the lysis of fruits or bunches of mandarin

| | Experiment | | |
| Strain | a | b | c |
|---|---|---|---|
| *Cryptococcus sp.* N6 | ++ | ++ | + |
| *Cryptococcus albidus* IFO0378 | − | NT | NT |
| *Saccharomyces cerevisiae* IFO2347 | − | NT | NT |
| Sterile Water | − | − | − |

++: Remarkably lysed and the original shape was not remained;
+: The original shape was not remained and was converted to small fragments;
−: Never lysed;
NT: Not tested These results demonstrate that the pectinases produced by *Cryptococcus* sp. N6 strain are remarkably suitable for hydrolyzing pericarps of fruits and that a good result can be obtained by using either *Cryptococcus* sp. N6 strain itself or the supernatant of its culture is used.

Example 11

Determination of the Specific Activity of p36 and p40

The specific activities of p36, p40, one commercially available polygalacturonase (Sigma, P-3340) and three pectinases (Sigma, P-4716, P-2401, Calbiochem, 441201) were determined. The determination was conducted based on the change in $A_{276}$ value when the reaction was conducted according to the method described in Example 7 at 20° C. for 10 minutes or at 40° C. for 15 minutes. Each commercially available enzyme was used immediately after purchase at its newest state, namely at the highest state in its enzymatic activity. The amount of each enzyme was quantified using Protein Assay supplied by Bio-Rad. The specific activity was calculated as units per 1 μg of the protein. The results are shown in Table 5.

Figure 10:
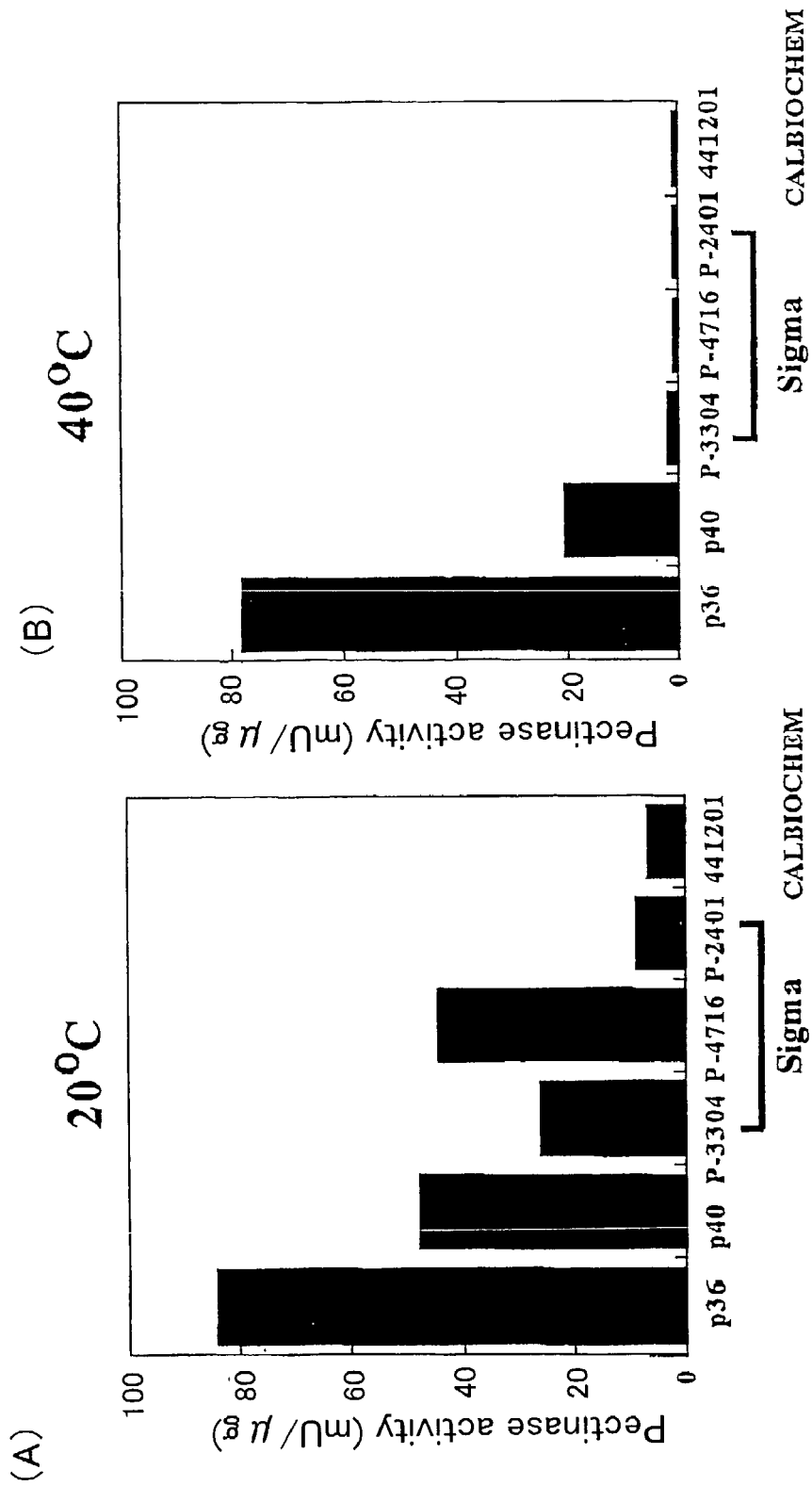
FIG. 10 is the graph showing the comparison of the activity of p36 or p40 with that of the marketed pectinase or galacturonase at 20° C. (A) or 40° C. (B). The longitudinal axis indicates milli-units (mU) per 1 μg of protein, where $1U=A_{276}/min$.

The results showed that p36 had much higher specific activity than any tested enzymes at 20° C. and 40° C., ant that p40 had the highest activity among 3 enzymes tested at 20° C. and had much higher specific activity than 4 enzymes compared at 40° C. (FIG. 10).

TABLE 5

Comparison of the specific activities of p36 and p40 with the commercially available enzymes

| | Specific Activity | |
| --- | --- | --- |
| Enzyme | 20° C. (mU/μg protein) | 40°C. (mU/μg protein) |
| p36 | 84.0 | 78.0 |
| p40 | 48.0 | 21.0 |
| P-3304 (Sigma) | 26.5 | 1.9 |
| P-4716 (Sigma) | 44.6 | 1.2 |
| P-2401 (Sigma) | 9.0 | 1.2 |
| 441201 (CALBIOCHEM) | 7.0 | 1.2 |

1 U = $A_{276}$/min.

---

What is claimed is:

1. An isolated pectinase which (a) comprises an N-terminal amino acid sequence of SEQ ID NO: 6 (b) is tolerant to copper ion at a concentration of up to 10 mM and (c) is produced by yeast strain N6 deposited under the accession No. FERM BP-6998.

2. The isolated pectinase according to claim 1, which has the following properties:
   i) an optimum pH of about 5.0;
   ii) an optimum temperature of about 40° C.;
   iii) a molecular weigh of about 36 k as measured by SDS-polyacrylamide gel electrophoresis.

3. The isolated pectinase according to claim 1, which has the following properties:
   i) an optimum pH of about 5.0;
   ii) an optimum temperature of about 50° C.;
   iii) a molecular weigh of about 40 k as measured by SDS-polyacrylamide gel electrophoresis.

4. The isolated pectinase according to claim 1, which has the N-terminal amino acid sequence of SEQ ID NO: 6.

5. A method of making the pectinase according to claim 1, comprising culturing a yeast *Cryptococcus* sp. capable of growing in the presence of copper ion at a concentration of up to 50 mM;

isolating the pectinase.

6. The method of claim 5, wherein the yeast is strain N6 deposited under the accession No. FERM BP-6998.

7. A method of hydrolyzing pectins, comprising contacting a pectin are reacted with the pectinase according to claim 1.

8. A method of producing a galacturonate, comprising:

reacting the pectinase according to claim 1 with a pectin-containing substrate; and, recovering galacturonate from the resulting lysate.

9. A method of producing vitamins, comprising:

reacting the pectinase according to claim 1 with a pectin-containing substrate; and, recovering vitamins from the resulting lysate.

* * * * *